United States Patent [19]

Goodale et al.

[11] Patent Number: 5,417,925
[45] Date of Patent: May 23, 1995

[54] CAPILLARY AND CAPILLARY RETAINING SYSTEM

[75] Inventors: David L. Goodale, Yorba Linda; George I. Reeves, Fullerton, both of Calif.

[73] Assignee: Beckman Instruments, Inc., Fullerton, Calif.

[21] Appl. No.: 71,832

[22] Filed: Jun. 3, 1993

Related U.S. Application Data

[63] Continuation of Ser. No. 48,709, Apr. 16, 1993, abandoned.

[51] Int. Cl.⁶ .............................................. B01L 11/00
[52] U.S. Cl. .................................... 422/103; 422/100; 422/104; 204/180.1; 204/299 R
[58] Field of Search ................. 422/99, 100, 103, 104; 204/180.1, 183.3, 299 R

[56] References Cited

U.S. PATENT DOCUMENTS

| | | | |
|---|---|---|---|
| 3,779,083 | 12/1973 | Ayres et al. | 422/100 X |
| 3,867,271 | 2/1975 | Hoefer | 204/299 R X |
| 4,048,049 | 9/1977 | Hoefer | 204/299 R |
| 4,375,401 | 3/1983 | Catsimpoolas | 204/299 R X |
| 4,788,150 | 11/1988 | Nelson | 436/45 |
| 5,045,172 | 9/1991 | Guzman et al. | 204/299 R |
| 5,110,431 | 5/1992 | Moring | 204/299 R X |
| 5,126,023 | 6/1992 | Huang et al. | 204/299 R X |
| 5,173,163 | 12/1992 | Tehrani | 204/299 R |
| 5,202,010 | 4/1993 | Guzman | 204/299 R |
| 5,207,886 | 5/1993 | Lauer et al. | 204/299 R |
| 5,227,138 | 7/1993 | Boyd et al. | 422/99 X |

FOREIGN PATENT DOCUMENTS

0339779A2 3/1989 European Pat. Off. .

*Primary Examiner*—Lyle A. Alexander
*Assistant Examiner*—Maureen M. Wallenhorst
*Attorney, Agent, or Firm*—William H. May; Arnold Grant; Sheldon & Mak

[57] ABSTRACT

A capillary and capillary retaining system including a capillary assembly having first and second end holders. The first and second end holders are adapted to be received by first and second retainers. The first end holder may include protruding portions and the first end retainer includes clips to receive the protruding portions. The second end holder may include opposite recesses and the second retainer is adapted to receive optical cables that are received within the recesses to retain the second end holder. Locks retained by the second end retainer cooperate with grooves in the optical cables to retain the optical cables.

29 Claims, 4 Drawing Sheets

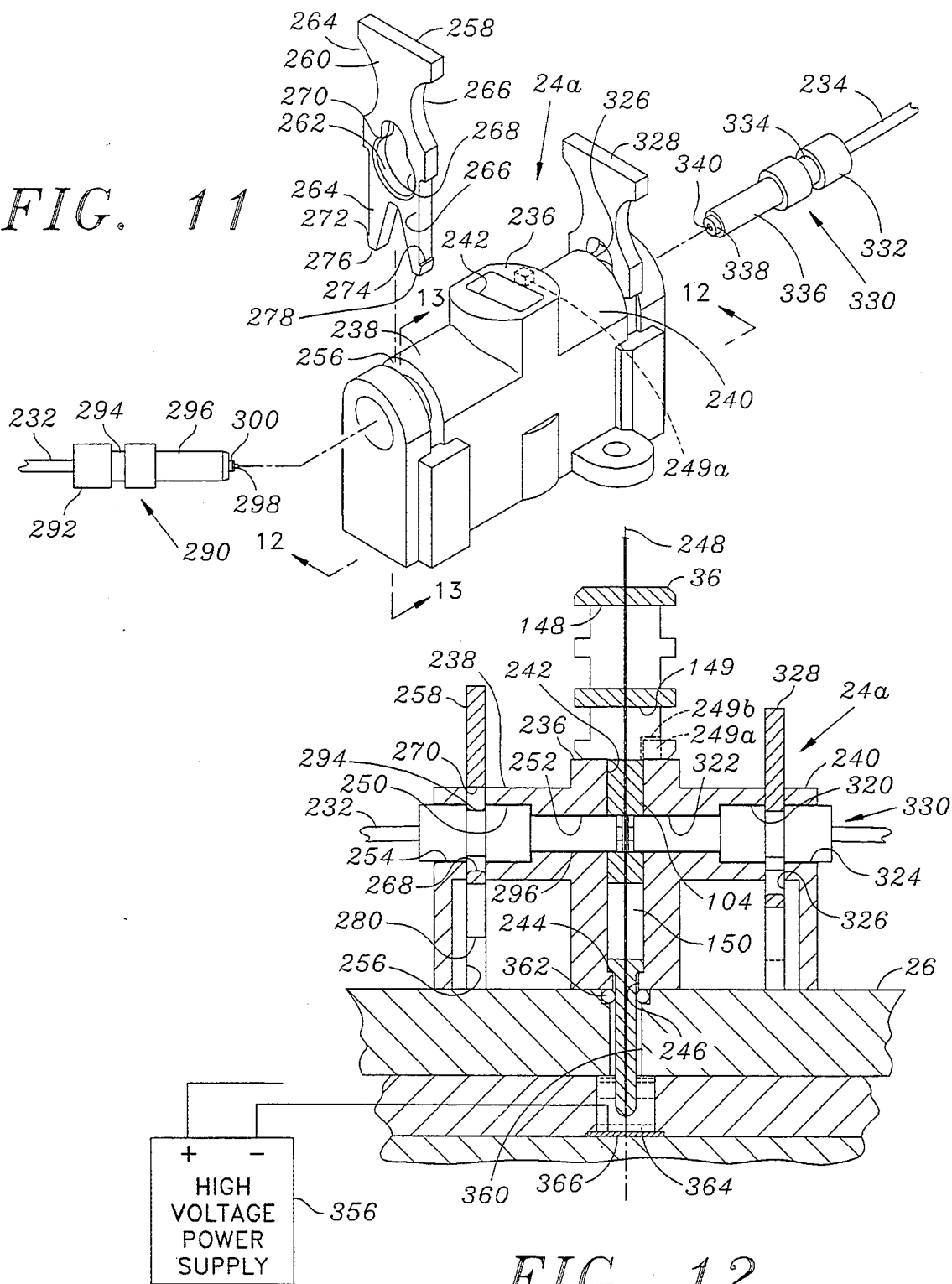

CAPILLARY AND CAPILLARY RETAINING SYSTEM

RELATED APPLICATIONS

This application is a continuation of U.S. patent application Ser. No. 08/048,709, filed Apr. 16, 1993, and now abandoned.

The present application is related to the following applications that are commonly assigned and filed concurrently herewith, and which are incorporated herein by reference:

U.S. patent application Ser. No. 08/072,202, filed June 3, 1993 and now U.S. Pat. No. 5,356,525 issued Oct. 18, 1994, and U.S. patent application Ser. No. 08/071,831, filed Jun. 3, 1993.

FIELD

The present application is related to the field of capillary electrophoresis.

BACKGROUND

The value of capillary electrophoresis as a separation and analytical technique has been recognized for some time. In capillary electrophoresis, a small tube or capillary is filled with an electrically conductive fluid, or buffer. A small quantity of a sample to be analyzed is introduced into one end of the capillary bore the ends of the capillary are placed into separate reservoirs of buffer, and a direct current high voltage is applied to the ends of t,e capillary by means of electrodes positioned in the buffer reservoirs, causing a small current to flow through the capillary.

With the correct polarity applied across the capillary, the sample begins to migrate toward the other end of the capillary. As this migration occurs, different molecules in the sample travel at different rates, causing the sample to become separated into bands of these different molecules. These bands or groups of different molecules are detected near the other end of the capillary by, for example, passing a perpendicular light beam through the bore of the capillary. Changes to the light beam, such as absorbance caused by the different molecules, are detected as the separated molecules pass through the beam, thus identifying the different molecules or the classes or categories of molecules in the sample and the relative concentration of such molecules.

Capillary electrophoresis analyzers typically use a single capillary to perform an analysis. For example, European Patent Application number 89302489.3, publication number 0,339,779 A2, corresponding to U.S. patent application Ser. No. 188,773, filed Apr. 29, 1988 (Burolla) describes an automated capillary electrophoresis apparatus using a single capillary, as does U.S. Pat. No. 5,045,172 to Guzman. To increase throughput, however, a plurality of capillaries may be utilized in parallel, thus performing a corresponding plurality of capillary electrophoresis analyze simultaneously. An analyzer employing parallel capillaries is disclosed, for example, in U.S. patent application Ser. No. 07/916,308, filed Jul. 17, 1992, now abandoned and entitled "Multi-Channel Capillary Electrophoresis Systems."

In such an analyzer, there is a need for easy replacement of the capillaries. Such replacement should be possible without the use of special tools. Further, the capillaries should occupy a relatively small volume within such an analyzer, and thus the capillaries should be as closely spaced as possible while retaining each capillary in a fashion that allows replacement by hand. Due to the closely spaced nature of such capillaries, there is also a need for capillaries that can be easily replaced in such a confined space with relatively little manipulation, which is particularly important given the extremely small diameter of such capillaries.

Thus, there is a need for capillaries and a capillary retaining system that is easy to use, can be operated by hand without the need for special tools, that readily lends itself to closely-spaced capillaries, and that requires a relatively limited amount of manipulation to remove and replace capillaries.

SUMMARY OF THE INVENTION

The present invention satisfies these needs. In accordance with the present invention, a capillary assembly includes a capillary tube and first and second holders proximate first and second ends of the capillary tube. The first holder has protruding portions on opposite sides of a body. The second holder includes a body holding a portion of the capillary tube. The second holder includes windows formed in opposite sides of the body with the windows exposing a portion of the capillary tube.

The protruding portions may by cylindrical. The first holder may include a flat portion and a stop that defines an area between the protruding portions. The stop is of sufficient size to be grasped between the fingertips of a user. The first holder may further include orientation means such as a notch or other structure formed into an edge of the holder.

The present invention also contemplates a capillary retaining system. Such a system may include a capillary assembly, a first retainer for retaining a first end of the capillary assembly, and a second retainer for retaining a second end of the capillary assembly. Such a system may alternatively comprise the first and second retainers that are useful with a capillary assembly, but wherein the system does not include the capillary assembly itself. As a further alternative, such a system may also include a capillary assembly useful with first and second retainers, but wherein the system does not include the first and second retainers.

The capillary assembly may include first and second holders. The first retainer includes means for removably retaining the first holder, and the second retainer includes means for removably retaining the second holder. In one embodiment, the first retainer includes a base an opening in the base, and clips fixed with respect to the base. The clips include engaging means for releasably engaging protruding portions of the first holder.

The second retainer may include in one embodiment a retainer body defining a central opening sized to receive the second holder. Opposite bores in the retainer body intersect the central opening and are sized to receive end barrels of an optical cable, the end barrel retaining optical fibers and defining reduced portions. Retainer clips or locks slidably carried by the second retainer include means for removably engaging the barrel reduced portions. Such means may comprise a collar, and the collar can be part of a keyhole-shaped opening in the retainer clips.

The first retainer can include orientation means that orients the first holder when it is received by the first retainer. The second retainer may likewise include such orientation means for similarly orientating the second holder when it is received by the second retainer.

The present invention also contemplates a method of using a capillary assembly, including installing the first holder of the capillary assembly in the first retainer, installing the second holder in the second retainer, installing first and second optical cable end barrels in the second retainer, the barrels being received by the second holder windows of the capillary assembly, and operating the second retainer locks to capture the reduced portion of each optical cable barrel by the lock.

BRIEF DESCRIPTION OF THE DRAWINGS

These and other advantages and aspects of the present invention will be apparent with reference to the Figures in which:

FIG. 11 is a perspective partially exploded view of a detection end retainer of the system of FIG. 1;

FIG. 12 is a partial cross-section view of the detection end retainer of FIG. 11 taken generally along line 12—12 thereof, but with a detection end holder and input and output optical cables installed and an input lock in an unlocked position and an output lock in a locked position;

DETAILED DESCRIPTION

Figure 1:
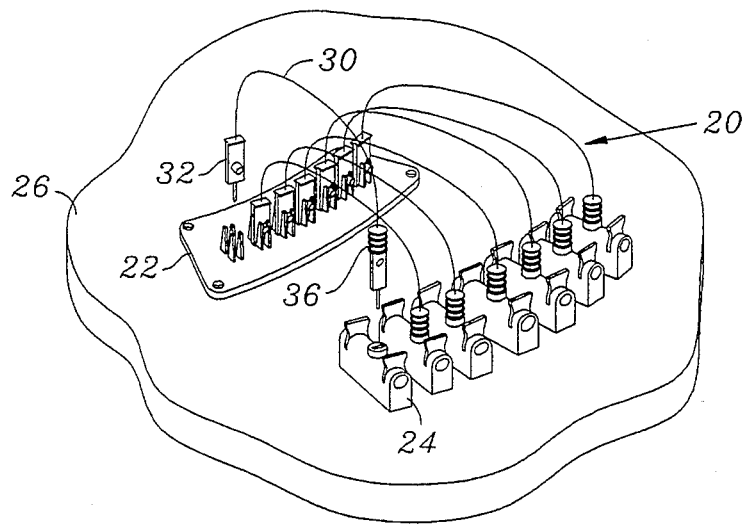
FIG. 1 is a perspective view of capillary assemblies and a capillary retaining system in accordance with the present invention.

With reference to FIG. 1, a plurality of capillary assemblies 20 may be removably retained by sample end retainers 22 and detection end retainers 24. The sample end retainers 22 and detection end retainers 24 may be, for example, fixed to a mounting platform or base 26 that is part of a capillary electrophoresis analyzer (not shown). A suitable electrophoresis analyzer is disclosed, for example, in U.S. Pat. No. 5,356,525 issued Oct. 18, 1994, and other such suitable analyzers will be apparent to those skilled in the art.

Figure 2:
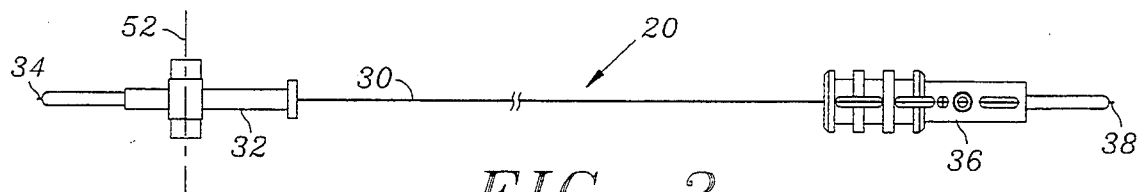
FIG. 2 is a view of a capillary assembly of FIG. 1.

With reference to FIG. 2, a capillary assembly 20 includes a capillary 30, a first or sample end holder 32 fixed proximate a sample induction end 34 of the capillary 30, and a second or detection end holder 36 fixed proximate a detection end 38 of the capillary 30. The capillary 30 is preferably conventional silica quartz glass formed with a thin conformal coating of a polyamide, having an inside diameter within a range of about five microns to two hundred microns and more particularly in a range of approximately twenty five microns to seventy five microns, and an outer diameter of about one hundred fifty microns to three hundred seventy five microns, respectively.

Figure 3:
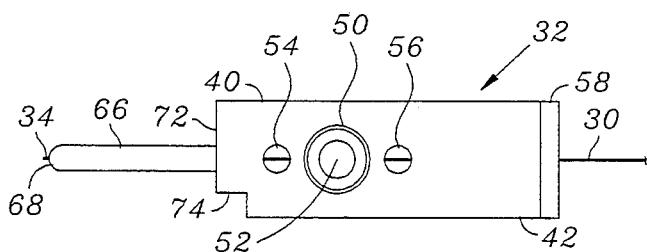
FIG. 3 is a side view of the sample end holder of the capillary assembly of FIG. 2.
Figure 4:
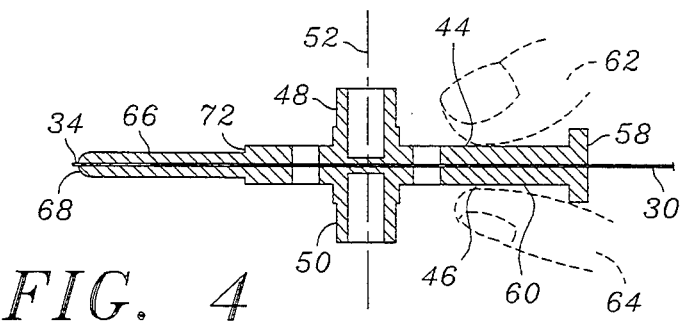
FIG. 4 is a section view of the sample end holder of the capillary assembly of FIG. 2.

The sample end holder 32 (FIGS. 2–4) has a body 40 including a generally flat portion 42 having opposite sides 44 and 46, and fastener bodies 48, 50 projecting from the opposite sides 44, 46. The fastener bodies 48, 50 are cylindrical and are coaxially aligned along axis 52. The axis 52 is perpendicular to and intersects the capillary 30. Openings 54, 56 in the flat portion 42 provide access to the capillary 30 so that the capillary 30 can be held in place during fabrication by, for example, molding of the sample end holder 32 onto the capillary 30. The openings 54, 56 also provide stress relief for the capillary 30 otherwise associated with the cooling of the sample end holder 32 material, preferably black plastic, during molding.

A stop 58 is formed at one end of the flat portion 42, the stop projecting perpendicularly with respect to the flat portion 42. An area 60 between the fastener bodies 48, 50 and the stop 58 provides a convenient gripping area between fingertips 62, 64 (shown in phantom is FIG. 4) of a user of the capillary assembly 20.

The body 40 also includes an inlet cylindrical portion 66 having a rounded end 68, the open sample induction end 34 of the capillary 30 extending slightly from the rounded end 68. An end or shoulder 72 is defined at the end of the flat portion 42 opposite from the end at which the stop 58 is formed, the end 72 having a notch 74 at one corner thereof.

Figure 6:
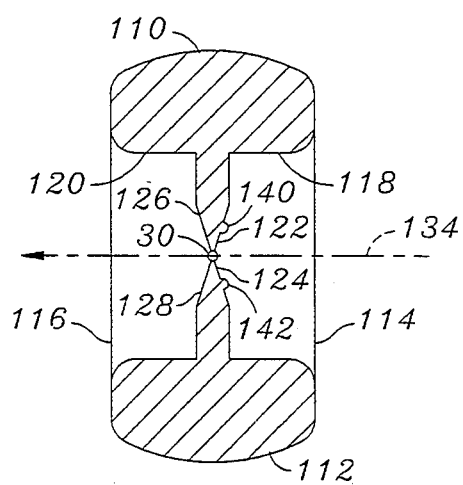
FIG. 6 is a section view of the detection end holder of FIG. 5 taken along line 6—6 thereof.
Figure 5:
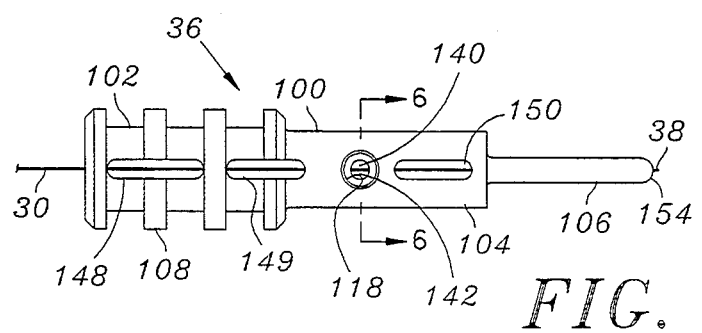
FIG. 5 is a side view of the detection end holder of the capillary assembly of FIG. 2.

The detection end holder 36 (FIGS. 5–7) has a body 100 having a handle portion 102, flat portion 104 and an outlet cylindrical portion 106. The handle portion 102 is cylindrical and includes ribs 108 that facilitate grasping between the finger tips of a user. The flat portion 104 has rounded edges 110, 112 and flat opposite surfaces 114, 116. Aligned opposing cylindrical input and output recesses 118, 120, respectively, are formed in the flat portion 104 and tapered surfaces 122, 124 and 126, 128, centered at the bottoms of the recesses 118 and 120, respectively, expose a length 130 of the capillary 30.

Figure 7:
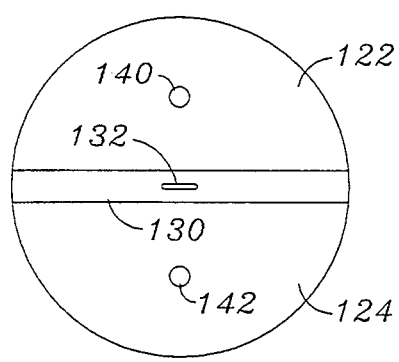
FIG. 7 is an enlarged view of the bottom of the input recess of FIG. 6.

Opposite windows are formed in the coating of the capillary 30, one of the windows 132 being illustrated in FIG. 7. The windows form an optical path 134 through the capillary 30. In the embodiment disclosed herein, the windows are about 0.001 inch by 0.008 inch. A capillary assembly utilizing windows of the type disclosed herein is described in U.S. patent application Ser. No. 07/917,640, filed Jul. 17, 1992 in the name of Waska et al, entitled "Capillary Electrophoresis Detection," now U.S. Pat. No. 5,312,535 issued May 17, 1994 which is incorporated herein by reference.

Targets 140, 142 are formed on the tapered surfaces 122, 124, the targets 140, 142 taking the form of small bumps or protrusions. The targets 140, 142 are at predetermined distances from the exposed length 130 of the capillary 30 and provide alignment references for use in removing the capillary 30 coating to form the opposing windows by, for example, burning off using a laser.

Elongated through openings 148, 149 and 150 in the detection end holder 36 are used to hold and position the capillary 30 during fabrication by, for example, molding of the detection end holder 36 onto the capillary 30. As with the openings 54, 56 in the sample end holder 32, the elongated openings 148, 149 and 150 also provide stress relief for the capillary 30 that might otherwise be associated with the cooling of the detection end holder 36 material, preferably black plastic, during molding.

The outlet cylindrical portion 106 is similar to the sample induction end cylindrical portion 66 and likewise includes a rounded end 154. The open detection end 38 extends slightly beyond the rounded end 154.

Figure 8:
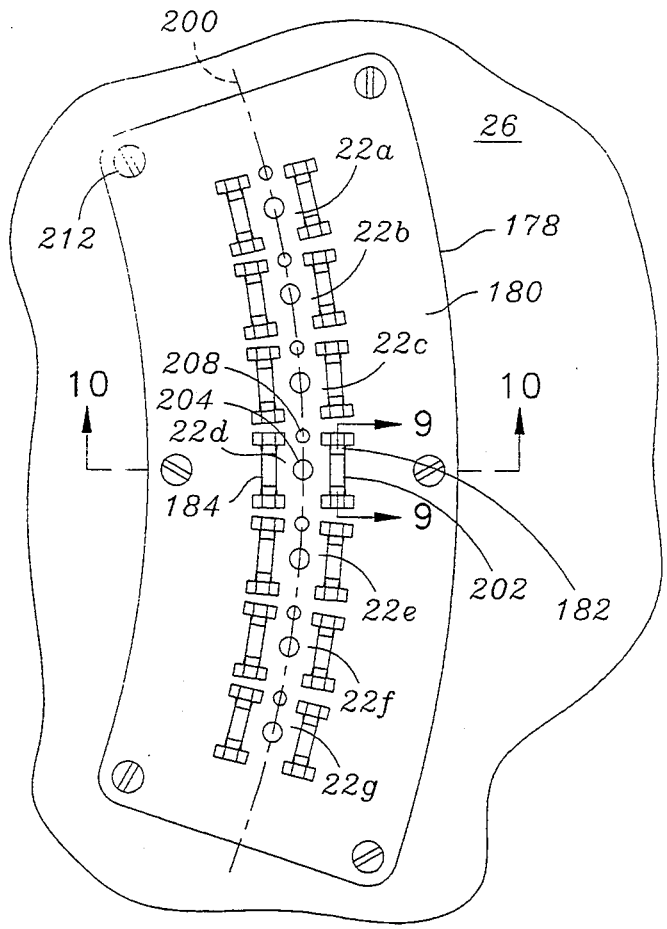
FIG. 8 is a top view of a sample end retainer of FIG. 1.
Figure 9:
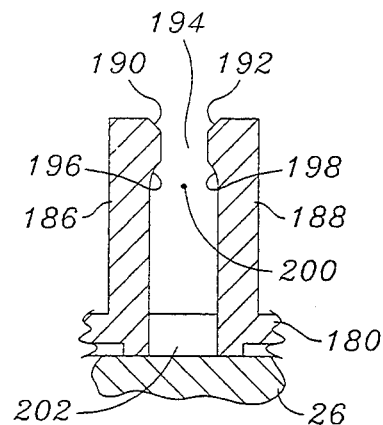
FIG. 9 is a cross-section view of the sample end retainer of FIG. 8 taken along line 9—9 thereof.

In the embodiment disclosed herein, the sample end retainers 22 are formed in a single arcuate header 178 (FIG. 8). The header 178 has a flange 180, the header 178 forming seven sample end retainers 22a–22g. The fourth sample end retainer 22d is typical of the others, and has two clips 182, 184, each of which has opposing flexible arms 186, 188, illustrated in FIG. 9 with respect to the first clip 182. The arms 186, 188 project from the flange 180 and include opposing enlarged ends 190, 192 that form a reduced entrance 194 and engagement surfaces 196, 198. The engagement surfaces 196, 198 share a common radius center point 200 and a slot 202 through the flange 180 is formed between the arms 186, 188 to increase the flexibility of the arms 186, 188.

Figure 10:
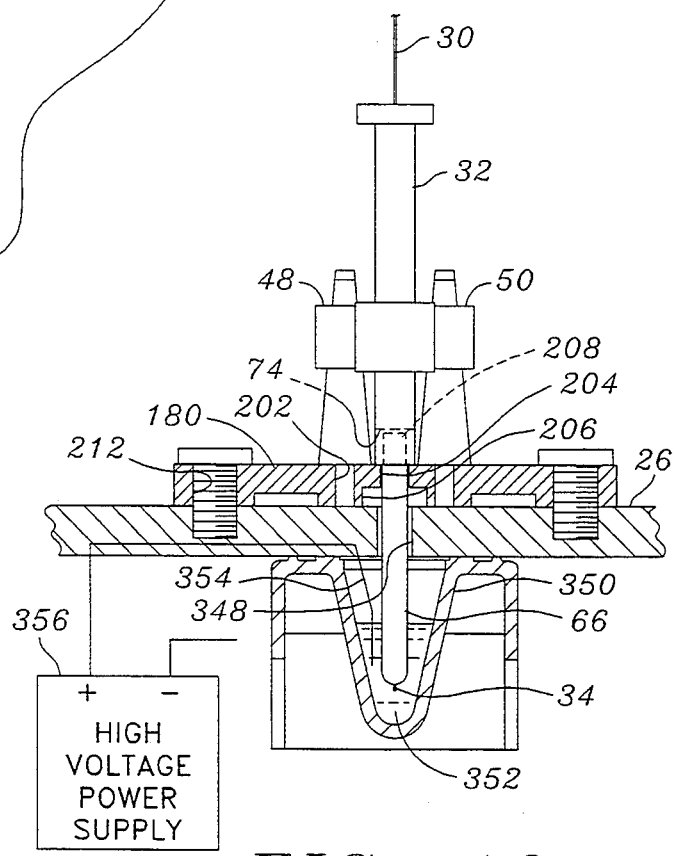
FIG. 10 is a partial cross-section view of the sample end retainer of FIG. 8 taken along line 10—10 thereof.

The two clips 182, 184 are on opposite sides of a round opening 204 (FIG. 10), the opening 204 including an enlarged portion 206 formed in the opposite side of the flange 180. A raised boss 208 between the clips 182, 184 projects from the flange 180. The boss 208 is to one side of the opening 204 and is sized to be received within the notch 74 when the sample end holder 32 is removably retained by the sample end retainer 22 as is described below. In the embodiment illustrated in FIG. 8, the sample end retainers 22a–22g are aligned in an arcuate path 210.

The flange 180 may include a plurality of openings 212 that can be used for fastening the header 178 and thus the sample end retainers 22a–22g to the base 26.

The detection end retainers 24 (FIGS. 11 and 12) are adapted to retain the capillary assemblies 20 and input and output optical cables 232, 234. The detection end retainers 24 are typical and one of such retainers 24a is shown in FIG. 11. The detection end retainer 24a includes a holder portion 236 and input and output cable receivers 238, 240. The holder portion 236 has a vertical elongated opening 242 sized to receive the flat portion 104 of the detection end retainer 36, the elongated opening 242 having an end 244 with a round opening 246 sized to receive the outlet cylindrical portion 106. The round opening 246 is centered with respect to the elongated opening 242 with a central axis 248 common to both such that the flat portion 104 and the outlet cylindrical portion 106 can be received within the holder portion 236 with the outlet cylindrical portion 106 extending out of the round opening 246.

Figure 13:
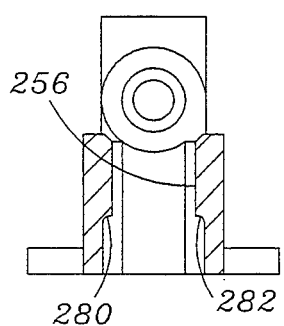
FIG. 13 is a partial cross-section view of the detection end retainer of FIG. 11 taken along line 13—13 thereof.

The input cable receiver 238 defines an input bore 250 having a reduced portion 252 and a larger portion 254, the reduced portion 252 being proximate the elongated opening 242. A vertical slot 256 intersects the larger portion 254 and is sized to receive a input lock 258. The input lock 258 has a handle portion 260, a keyhole opening 262, and legs 264, 266. The handle portion 260 has indentations 266 sized to receive the fingers of a user (not shown). The keyhole opening 262 has a larger opening 268 (as illustrated in FIG. 11) and a smaller collar or key portion 270. The legs 264, 266 each include outward shoulders 272, 274 proximate ends 276, 278. The outward shoulders 272, 274 are adapted to engage inward shoulders 280, 282 (FIG. 13) in the slot 256, allowing the input lock 258 to be movably retained within the slot 256.

The input bore 250 receives an end connector 290 of the input optical cable 232. The end connector 290 has a barrel 292 with a circumferential groove 294 and a tube 296 about the end of an input optical fiber 298. A sleeve 300 projects from the end of the tube 296 and crimps the optical fiber 298 in place.

The output receiver 240 is similar to the input receiver 238, and has an output bore 320 with reduced and larger portions 322, 324 respectively, and slot 326 retaining an output lock 328. The output bore 320 is adapted to receive an end connector 330 of the output optical cable 234, the end connector 330 including a barrel 332, groove 334, tube 336 and sleeve 338 about an output fiber 340 in a similar fashion to the input end connector 290.

The detection end holder 36 may also be keyed with respect to the elongated opening 242 by the use, for example, of a boss 249a formed at the side of the elongated opening 242, which cooperates with a notch 249b formed in the handle portion 102. The boss 249a and notch 249b are shown in phantom in FIGS. 11 and 12, and function in a similar fashion to the boss 208 and notch 74 associated with the sample end retainer 22d and sample end holder 32 described above.

In use, a plurality of the capillary assemblies 20 is installed into, for example, the sample end retainer 22d and the typical detection end retainer 24. To install one of the capillary assemblies 20 onto the sample end retainer 22, the cylindrical portion 66 of the sample end holder 32 (FIG. 10) is inserted through the opening 204 in the flange 180 and an aligned opening 348 in the base 26. The sample end retainer 22 is urged toward the flange 180 and the fastener bodies 48, 50 are pressed through the reduced entrance 194, flexing the arms 186, 188 (and corresponding arms for clip 184) aside. With the shoulder 72 against the flange 180, the fastener bodies 48, 50 are engaged by the engagement surfaces 196, 198 (and similar engagement surfaces for the clip 184) as shown in phantom in FIG. 9, retaining the sample end holder 32 within the sample end retainer 22d. The boss 208 and notch 74 cooperate to index or orient the sample end holder 32 with respect to the sample end retainer 22d.

The sample induction end 34 may be, for example, disposed within a well 350 containing a dilute sample 352 to be analyzed. An electrode 354 is also in contact with the sample 352 and is connected to a high voltage power supply 356, shown in simplified block from in FIG. 10.

The detection end holder 36 of the capillary assembly 20 is installed into a respective detection end retainer 24 by inserting the flat portion 104 into the elongated opening 242 with the outlet cylindrical portion 106 passing through the round opening 246 in the holder portion 236 and through a manifold opening 360 in the base 26 that is aligned with the round opening 246. An o-ring seal 362 seals the outlet cylindrical portion 106 within a conduit in which is disposed a liquid buffer 364 in which the detection end 38 is held. An electrode 366 is connected to the other potential supplied by the high voltage power supply 356, providing an electrophoresing voltage as is well known in the art between the sample 352 and the buffer 364.

The input lock 258 is raised, the shoulders 272, 274 engaging the inward shoulders 280, 282 and aligning the center of the larger opening 268 with the centerline of the bore 250. The input optical cable 232 in inserted into the bore 250, the tube 296 being received within the input recess 118 and aligning the input fiber 298 with the optical path 134 through the window 132. The input lock 258 is operated to engage the collar or key portion 270 and the groove 294, thus retaining the input optical cable 232 within the detection end holder 36.

Similarly, the output optical cable 234 is installed into the detection end retainer 24a, the tube 336 engaging the output recess 120 and aligning the output fiber 340 with the optical path. The output lock 328 is operated to engage the groove 334. With the tubes 296 and 336 engaging the input and output recesses 118, 120, the detection end holder 36 is secured within the detection end retainer 24a.

Additional capillary assemblies 20 are similarly installed. Individual wells 350 may be provided for each of the capillary assemblies 20, and the conduit 360 may be common beneath the detection end retainers 24, providing the buffer 364 to the detection end 38 of each of the capillary assemblies 20.

Removal of the capillary assembly 20 is effected by pulling the sample end holder 32 free from the sample end retainer 22, the arms 186, 188 flexing to release the fastener bodies 48, 50. The input and output locks 258, 328 are raised, the input and output cables 232, 234 are removed, and the detection end holder 36 is removed from the detection end retainer 24.

It is to be appreciated that the present invention contemplates that a single capillary assembly 20 may be retained by a single sample end retainer 22 and a single detection end retainer 24. Such may be useful, for example, if an analyzer is designed to provide a single capillary analysis at a given time. The invention also contemplates that a plurality of capillaries may be conveniently retained as illustrated in FIG. 1, thus allowing multiple parallel capillary electrophoretic analyses to be performed simultaneously in a single analyzer.

Figure 14:
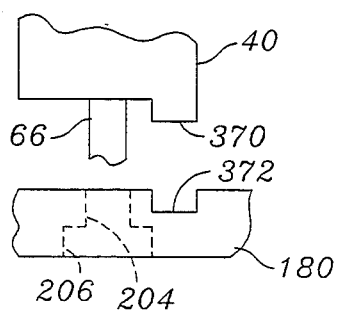
FIG. 14 is a partial side view of an alternative form of orientation means useful in the sample end holder of FIG. 3.

Moreover, the boss 208 and notch 74, as well as the boss 249a and notch 249b, are optional. For example, the boss 208 and notch 74 need not be used where orientation of the sample end holder 32 is not important with respect to a sample end retainer 22. Similarly, the boss 249a and notch 249b need not be used if the orientation of the windows through the capillary 30 are not important when the detection end holder 36 is installed in the detection end retainer 24. Additionally, other forms of orientation means can be used. For example, the notch 74 can be replaced by a protrusion 370 in the body 40 (FIG. 14) that is adapted to mate with a corresponding recess 372 in the sample end retainer flange 180. Similar structure can likewise be utilized on the detection end holder 36 and the detection end retainer 24.

The present invention is not to be limited to the particular embodiment disclosed herein but is instead to be accorded the fully scope of the appended claims and all equivalents thereto.

We claim:

1. A capillary assembly comprising:
   (a) a capillary tube having a first end and a second end;
   (b) a first holder holding a portion of the capillary tube proximate the first end, the first holder comprising a cylindrical portion proximate the first end and a flat portion extending from the cylindrical portion to an end of the first holder remote from the first end of the capillary tube, the flat portion comprising an end and stops projecting from the end substantially perpendicular to the flat portion, the first holder further comprising coaxially aligned cylindrical protrusions for cooperation and removable engagement with a capillary retaining system; and
   (c) a second holder holding a portion of the capillary tube proximate the second end, wherein the second holder is suitable for cooperation and removable engagement with the capillary retaining system.

2. A capillary assembly as in claim 1 wherein the protrusions protrude from the flat portion, the protrusions and the stops defining an area therebetween of sufficient size to be gripped between fingertips of a user.

3. A capillary assembly comprising:
   (a) a capillary tube having a first end, a second end, an inside diameter of between about 25 microns to about 75 microns, a first open end, and a second open end;
   (b) a first holder holding a portion of the capillary tube proximate the first end, the first holder comprising a cylindrical portion proximate the first end and a flat portion extending from the cylindrical portion remote from the first end of the capillary tube, the flat portion comprising an edge adjacent the cylindrical portion and orientation means formed into the edge, the flat portion further comprising opposite sides and cylindrical protrusions on the opposite sides of the flat portion for cooperation with and removable engagement with a capillary retaining system; and
   (c) a second holder holding a portion of the capillary tube proximate the second end, the second holder having opposite sides and comprising windows formed in the opposite sides, the windows exposing a portion of the capillary tube, the exposed portion of the capillary tube having walls substantially transparent to light energy, wherein the second holder is suitable for cooperation with and removable engagement with the capillary retaining system.

4. A capillary assembly as in claim 3 wherein the orientation means includes a notch formed into the flat portion edge of the first holder.

5. A capillary assembly as in claim 3 wherein the orientation means includes a protrusion formed into the flat portion edge of the first holder.

6. A capillary assembly as in claim 3 wherein the second holder further comprises: an outlet cylindrical portion proximate the second end of the capillary tube, and a second holder flat portion, wherein the second holder flat portion comprises: (i) an edge adjacent the outlet cylindrical portion, and (ii) orientation means formed proximate the edge of the second holder flat portion.

7. A capillary assembly as in claim 6 wherein the second holder orientation means comprises a notch formed into the second holder flat portion.

8. A capillary assembly as in claim 6 wherein the second holder orientation means comprises a protrusion formed into the second holder flat portion.

9. A capillary assembly as in claim 6 wherein the orientation means of the first holder and the orientation means of the second holder each comprise notches formed into the flat portions of the first and the second holders respectively.

10. A capillary retaining system suitable for receiving optical cables having end barrels retaining optical fibers, the retaining system comprising:

(a) a capillary assembly comprising:
  (i) a capillary tube having a first end and a second end,
  (ii) a first holder holding a portion of the capillary tube proximate the first end, the first holder comprising protrusions for cooperation with and removable engagement with the capillary, retaining system, and
  (iii) a second holder holding a portion of the capillary tube proximate the second end, the second holder comprising a flattened portion having opposite sides, the flattened portion comprising opposite aligned recesses formed in the opposite sides of the flattened portion, the recesses being sized to receive end barrels of optical cables, the end barrels retaining optical fibers, wherein the recesses expose the capillary tube, and wherein the second holder is suitable for cooperation with and removable engagement with the capillary retaining system;
(b) a first retainer for releasably engaging the first holder, the first retainer comprising a base, an opening in the base, and clips disposed on the base proximate the opening, the clips comprising engaging means for releasably engaging the protrusions on the first holder; and
(c) a second retainer for releasably engaging the second holder, the second retainer comprising: (i) a retainer body defining a central opening sized to receive the second holder flattened portion, (ii) opposite bores defined in the retainer body and intersecting the central opening, and sized to receive end barrels of optical cables, the end barrels retaining optical fibers, and (iii) retainer locks slidably carried by the second retainer in secondary openings defined in the retainer body, the secondary openings intersecting the bores, wherein the retainer locks comprise means for removably engaging end barrels of optical cables.

11. A capillary retaining system as in claim 10 wherein the chips of the first retainer comprise opposing flexible arms and wherein the engaging means comprises opposing enlarged ends of the flexible arms.

12. A capillary retaining system as in claim 11 wherein the first holder comprises a shoulder formed on the holder between the first end of the capillary tube and the protrusions, wherein the protrusions are cylindrical members, and wherein the opposing flexible arms of the clips are sized to resiliently urge the opposing enlarged ends against the cylindrical members when the first holder is received by the first retainer such that the shoulder is urged against the base of the first retainer.

13. A capillary retaining system as in claim 10 wherein the first retainer and the first holder include cooperative orientation means for orienting the first holder with respect to the first retainer when the first holder is removably retained by the first retainer.

14. A capillary retaining system as in claim 13 wherein the cooperative orientation means includes a boss projecting from the base of the first retainer and wherein the first holder includes a notch formed in the holder between the first end of the capillary tube and the protrusions, wherein the notch is adapted to receive the boss.

15. A capillary retaining system as in claim 14 wherein the clips comprise a first set of clips and a second set of clips, the first and the second set of clips disposed on opposite sides of the opening in the base respectively, wherein the boss is formed to one side of the opening in the base, and wherein the first holder further includes a flat portion, the flat portion having opposite sides and an edge, wherein the notch is formed in the edge of the flat portion.

16. A capillary retaining system as in claim 15 wherein the protrusions of the first holder are on the flat portion.

17. A capillary retaining system as in claim 10 wherein the first holder further comprises a cylindrical portion proximate the first end of the capillary tube and remote from the protrusions, and wherein the opening in the base of the first retainer is sized to receive the cylindrical portion.

18. A capillary retaining system suitable for receiving optical cables having end barrels retaining optical fibers, the retaining system comprising:
(a) a capillary assembly comprising:
  (i) a capillary tube having a first end and a second end,
  (ii) a first holder holding a portion of the capillary tube proximate the first end, the first holder comprising protrusions for cooperation with and removable engagement with the capillary retaining system, and
  (iii) a second holder holding a portion of the capillary tube proximate the second end, the second holder comprising a flattened portion having opposite sides, the flattened portion comprising opposite aligned recesses formed in the opposite sides of the flattened portion, the recesses being sized to receive end barrels of optical cables, wherein the recesses expose the capillary tube, and wherein the second holder is suitable for cooperation with and removable engagement with the capillary retaining system;
(b) a first retainer for releasably engaging the first holder, the first retainer comprising a base, an opening in the base, and clips disposed on the base proximate the opening, the clips comprising engaging means for releasably engaging the protrusions on the first holder; and
(c) a second retainer for removably retaining the second holder.

19. A capillary retaining system suitable for receiving optical cables having end barrels retaining optical fibers, the retaining system comprising:
(a) a capillary assembly comprising:
  (i) a capillary tube having a first end and a second end,
  (ii) a first holder holding a portion of the capillary tube proximate the first end, the first holder comprising protrusions for cooperation with and removable engagement with the capillary retaining system, and
  (iii) a second holder holding a portion of the capillary tube proximate the second end, the second holder comprising a flattened portion having opposite sides, the flattened portion further comprising opposite aligned recesses formed in the opposite sides of the flattened portion, the recesses being sized to receive end barrels of optical cables, wherein the recesses expose the capillary tube, and wherein the second holder is suitable for cooperation with and removable engagement with the capillary retaining system;
(b) a first retainer for removably retaining the first holder; and (c) a second retainer for releasably engaging the second holder, the second retainer comprising (i) a retainer body defining a central opening sized to receive the second holder flattened body portion, (ii) opposite bores defined in the retainer body and intersecting the central opening and sized to receive end barrels of optical cables, and (iii) retainer locks slidably carried by the second retainer in secondary openings defined in the retainer body, the secondary openings intersecting the bores, wherein the retainer locks comprise means for removably engaging end barrels of optical cables.

20. A capillary retaining system as in claim 19 wherein the engaging means of each of the second retainer locks comprises a collar.

21. A capillary retaining system as in claim 20 wherein each collar is included in a keyhole-shaped opening in the respective retainer lock having a larger portion and a smaller portion defining the collar in the retainer lock, the larger portion being sized to receive end barrels of optical cables.

22. A capillary retaining system suitable for receiving optical cables having end barrels retaining optical fibers, the retaining system comprising:
(a) a capillary assembly comprising:
  (1) a capillary tube having a first end and a second end;
  (2) a first holder fixed proximate the first end of the capillary tube, the first holder comprising a cylindrical portion proximate the first end of the capillary tube and a flattened portion proximate the cylindrical portion and remote from the first end of the capillary tube, the flattened portion having opposite surfaces, and wherein the first holder further comprises a fastener member on each of the opposite surfaces for cooperation with and removable engagement with a capillary retaining system; and
  (3) a second holder holding a portion of the capillary tube proximate the second end, the second holder comprising a flattened portion having opposite sides, the flattened portion further comprising opposite aligned recesses formed in the opposite sides of the flattened portion, the recesses being sized to receive end barrels of optical cables, wherein the recesses expose the capillary tube, and wherein the second holder is suitable for cooperation with and removable engagement with a capillary retaining system;
(b) a first retainer comprising a base, an opening in the base sized to receive the first holder cylindrical portion, and clips projecting from the base proximate the opening, the clips including means for releasably engaging the fastener members on the first holder; and
(c) a second retainer for releasably engaging the second holder, the second retainer comprising: (i) a retainer body defining a central opening sized to receive the second holder flattened portion, (ii) opposite bores defined in the retainer body and intersecting the central opening and sized to receive end barrels of optical cables, and (iii) retainer locks slidably carried by the second retainer in secondary openings defined in the retainer body, the secondary openings intersecting the bores, wherein the retainer locks comprise means for removably engaging end barrels of optical cables.

23. A capillary retaining system as in claim 22 wherein the first retainer and the first holder include cooperative orientation means for orienting the first holder with respect to the first retainer when the first holder is removably retained by the first retainer, wherein the orientation means of the first retainer comprises a boss projecting from the base of the first retainer, and wherein the orientation means of the first holder comprises a notch formed in the flattened portion of the first holder adjacent the cylindrical portion, wherein the notch is adapted to receive the boss.

24. A capillary retaining system as in claim 23 wherein the clips of the first retainer comprise a first set of clips and a second set of clips, the first and the second set of clips disposed on opposite sides of the opening in the base respectively, wherein the boss is formed to one side of the opening in the base, and wherein the first holder flattened portion has an edge, and the notch is formed in the edge of the flattened portion.

25. A capillary retaining system as in claim 22 wherein the system includes a plurality of capillary assemblies, a plurality of first retainers, and a plurality of second retainers.

26. The capillary retaining system of claim 25 further comprising a mounting surface, wherein the first retainers are disposed on the mounting surface substantially adjacent to one another, and wherein the second retainers are disposed on the mounting surface substantially adjacent to one another, whereby the plurality of capillary assemblies can be disposed in the retaining system adjacent to one another.

27. A capillary retaining system useful for receiving (i) optical cables having end barrels retaining optical fibers, and (ii) a capillary assembly, the capillary retaining system comprising:
a mounting surface;
a first retainer fixed to the mounting surface, the first retainer comprising a base, an opening in the base, and clips disposed on the mounting surface proximate the opening, the clips including engaging means for releasably engaging a first holder of a capillary tube, the capillary tube having a first end and a second end, and the first holder holding a portion of the capillary tube proximate the first end; and
a second retainer fixed to the mounting surface and having a retainer body defining a central opening sized to receive a second holder of a capillary tube, the capillary tube having a first end and a second end, and the second holder holding a portion of the capillary tube proximate the second end, opposite bores defined in the second retainer body and intersecting the central opening and sized to receive end barrels of optical cables, and retainer locks slidably carried by the second retainer in secondary openings defined in the retainer body, the secondary openings intersecting the bores, wherein the retainer locks comprise means for removably engaging end barrels of optical cables.

28. A system as in claim 27 wherein the mounting surface comprises: (i) means for retaining a first liquid aligned with the opening in the base of the first retainer, (ii) means for retaining a second liquid aligned with the second retainer central opening, and (iii) means for applying an electrophoresing voltage between the first and the second retainers.

29. A method of using a capillary assembly, the method comprising the steps of:

(a) selecting a capillary assembly comprising a capillary tube having a first end and a second end, the capillary assembly further comprising: (a) a first holder holding a portion of the capillary tube proximate the first end, the first holder comprising protrusions for cooperation with and removable engagement with a capillary retaining system, and (b) a second holder having a body, the body holding a portion of the capillary tube proximate the second end, wherein the body comprises windows formed in opposite sides of the body, the windows exposing a portion of the capillary tube, and wherein the second holder is suitable for cooperation with and removable engagement with the capillary retaining system;

(b) installing the first holder in a first retainer including a base, an opening in the base to receive the first holder, and clips disposed on the base proximate the opening, the clips including engaging means for releasably engaging the protrusions on the first holder;

(c) installing the second holder in a second retainer having a retainer body defining a central opening sized to receive the second holder, opposite bores defined in the retainer body and intersecting the central opening in the retainer body, and retainer locks slidably carried by the second retainer in secondary openings in the retainer body intersecting the bores, each retainer lock having a body including a retaining collar defined on the retainer lock body;

(d) installing a first optical cable in the second holder, the first optical cable including optical fibers, a connector having an end barrel holding an end of the optical fibers, the connector defining a reduced portion, the barrel being received within one of the second holder windows of the capillary assembly;

(e) installing a second optical cable in the second holder, the second optical cable including optical fibers, a connector having an end barrel holding an end of the optical fibers, the connector defining a reduced portion, the barrel being received within the other of the second holder windows of the capillary assembly; and (f) operating the retainer locks to capture the reduced portion of each optical cable connector by the retaining collars.

* * * * *